United States Patent [19]

Felman et al.

[11] Patent Number: 5,449,824
[45] Date of Patent: Sep. 12, 1995

[54] RECOVERY OF ORGANIC ACID SALTS FROM IMPURE PROCESS STREAMS BY ADDITION OF BASES

[75] Inventors: Steven W. Felman, Granger; Chetna Patel, Elkhart; Bhalchandra H. Patwardhan, Elkart; David J. Solow, Elkhart, all of Ind.

[73] Assignee: Haarmann & Reimer Corp., Elkhart, Ind.

[21] Appl. No.: 250,498

[22] Filed: May 27, 1994

Related U.S. Application Data

[63] Continuation-in-part of Ser. No. 87,656, Jul. 6, 1993, Pat. No. 5,352,825.

[51] Int. Cl.⁶ .............................................. C07C 51/42
[52] U.S. Cl. ................................................... 562/580
[58] Field of Search ......................................... 562/580

[56] References Cited

U.S. PATENT DOCUMENTS

| | | | |
|---|---|---|---|
| 1,906,065 | 3/1931 | Jenemann | 562/580 |
| 2,430,086 | 11/1947 | Staff | 562/580 |
| 4,137,260 | 1/1979 | Walter | 562/580 |
| 4,251,671 | 2/1981 | Alter et al. | 562/580 |
| 4,442,303 | 4/1984 | Mims | 562/580 |
| 4,720,577 | 1/1988 | Wojtch et al. | 562/513 |
| 4,851,574 | 7/1989 | Kulprathipanja | 562/580 |
| 4,924,027 | 5/1990 | Kulprathipanja | 562/580 |
| 4,994,609 | 2/1991 | Baniel et al. | 562/580 |
| 5,041,645 | 8/1991 | Alon et al. | 562/584 |
| 5,068,419 | 11/1991 | Kulprathipanja | 562/580 |
| 5,245,078 | 9/1993 | Maeda | 562/580 |

FOREIGN PATENT DOCUMENTS

| | | |
|---|---|---|
| 479084 | 4/1992 | European Pat. Off. |
| 2674848 | 9/1992 | France |
| 8164541 | 9/1983 | Japan |
| 868926 | 5/1961 | United Kingdom |
| 905817 | 9/1962 | United Kingdom |
| 709613 | 1/1980 | U.S.S.R. |

*Primary Examiner*—Paul J. Killos
*Attorney, Agent, or Firm*—Mary G. Boguslaski

[57] ABSTRACT

This invention provides an improved method for recovering an organic acid as a salt from various process streams by addition of a crystallizing base to a concentrated solution of neutralized organic acid. The addition of such a base causes crystallization of the salt. This process provides more efficient recovery of organic acid salt from a fermentation process stream than traditional crystallization and it may be used essentially as a one step purification process. The improved method is particularly applicable to the recovery of trisodium or tripotassium citrate from process streams produced in the fermentation and recovery of citric acid, with the addition of a crystallizing base such as sodium hydroxide, sodium carbonate, potassium hydroxide, or ammonia. The resulting product may be combined with an anticaking agent and/or dried to provide a particularly free flowing product.

10 Claims, No Drawings

RECOVERY OF ORGANIC ACID SALTS FROM IMPURE PROCESS STREAMS BY ADDITION OF BASES

Priority of application Ser. No. 08/087,656, filed on Jul. 6, 1993, now U.S. Pat. No. 5,352,825 is claimed under 35 USC 120. This application is also a CIP of 08/087,656 and of said patent.

BACKGROUND OF THE INVENTION

Organic acids salts, or the corresponding acids, am useful in the food, beverage, flavors and perfumery industries. The salt may be the preferred form for manufacture, with subsequent conversion to the acid as with organic acids produced for flavors and perfumery. In fermentation, the acid is commonly the fermentation product but the salt of such acid may be the desired end product. For example, citric acid salts, particularly the sodium salt, are suitable for use as chelators, flavor enhancers and buffers in pharmaceutical, food and industrial applications, where a higher pH is required than may be provided by citric acid. Potassium citrate is used in pharmaceuticals and in food products. These salts are typically prepared by neutralizing the organic acid solution with a base containing the appropriate cation, e.g. potassium hydroxide or sodium hydroxide.

Two principal acid recovery techniques which are used commercially at this time in conjunction with the fermentation of citric acid and salts thereof am solvent extraction as outlined in U.S. Pat. No. 4,275,234 to Baniel et al, and a lime-sulfuric acid process. Additional modifications of these recovery processes have been proposed in U.S. Pat. No. 4,994,609 to Baniel and Gonen and in EP 0 432 610 to Baniel and Eyal, respectively. EP 0 432 610 describes the concurrent production of citric acid and alkali citrates by subjecting the mother liquor, obtained from the crystallization of citric acid after the known lime-sulfuric recovery process, to extraction with a water-immiscible organic extractant that contains at least one organic amine and a liquid hydrocarbon. The resulting extract is separated and neutralized with an aqueous alkali citrate whereby an alkali citrate brine is formed. The extractant is recycled and the aqueous alkali citrate brine is processed for recovery of alkali citrate. The processing may comprise cooling, addition of alkali, e.g. gaseous ammonia and a combination of such operations. In the examples, ammonia is added to convert the monobasic citrate in solution to the dibasic citrate. On cooling to 40 degrees C. in a crystallizer, dibasic citrate crystallized out. If desired, in addition to or in lieu of adding alkali in the course of the processing of the alkali citrate brine, it is possible to add alkali during the neutralization operation. Baniel and Eyal describe a procedure for preparation of aqueous solutions of alkali citrates from which alkali citrates can be crystallized.

In addition, the literature describes many other techniques for the purification of citric acid from the impure fermentation broth. Among the literature references is published European Patent Application 0 167 957 owned by Hoechst AG which discloses a process for isolating water soluble acidic compounds by bringing a solution of the acid into contact with a weakly basic, adsorbent, ion exchange resin, preferably those containing tertiary amino groups, and then desorbing the acid with water and/or steam.

Offenlegungsschrift DE 3 502 924, owned by Benckiser GmbH, discloses a citric acid purification process involving membrane filtration, preferably ultrafiltration, together with adsorption of impurities on a non-ionic resin such as polystyrene or polyacrylamide and crystallization. U.S. Pat. No. 4,851,573, to Kulprathipanja et al discloses a method for separation of citric acid from its fermentation broth by contacting the broth with a water-insoluble macroreticular gel of a weakly basic anionic exchange resin possessing tertiary amine functional groups or pyridine functional groups and a cross-linked acrylic or styrene resin matrix. The citric acid is desorbed by water or dilute sulfuric acid.

Other methods which may be used to purify citric acid fermentation broths include ion exchange, nanofiltration. U.S. Pat. No. 5,032,686, to Duflot et al and assigned to Roquette, Freres, discloses a method for the recovery of citric acid from a liquor containing the same, by successively: 1) putting the liquor containing the citric acid in contact with a cationic resin in the hydrogen form for a duration sufficient to reach an optimal adsorption (approximately 90%) of the acid; and 2) treating the resin by elution whereby the fraction of eluate rich in purified citric acid is recovered. A preferred eluant is water at a temperature higher than 40 C.

Hubertus Juetten, in his thesis entitled "The Enhanced Crystallization of Dicarboxylic Acids in Electrolyte Solutions," Michigan State University, 1992, states in the abstract that generally, carboxylic acid fermentations utilize anaerobic conditions and base addition for pH control. The salts of carboxylic acids then produced must be converted to the free acids and recovered. He states that a process for the crystallization of carboxylic acids by means of salting-out with the electrolyte sulfuric acid has been developed. The work disclosed is primarily directed to the recovery of succinic acid from an aqueous solution of sodium succinate and sodium acetate. Juetten also discloses experiments on the salting out of citric acid, L-tartaric acid and DL malic acid from saturated solutions of pure acids in water by addition of sulfuric acid (page 25). No experiments were disclosed on the application of this process to fermentation broth. Juetten suggested that the salting out process could be used as a modification of the Berglund et al process (U.S. Pat. No. 5,034,105) which is described in the thesis, page 45, as a process for preparing a supersaturated solution of carboxylic acid from a fermentation broth. The anaerobic fermentation used to produce succinic acid operates optimally at pH's where salts of the organic acids rather than free acids are formed. Berglund provides an electrodialysis method whereby the mixed salt stream produced by such fermentation creates supersaturation in any system where the salt is more soluble than the acid. This process results in a mixture of two acids, succinic and acetic. Juetten provides a detailed proposal for the modification of the Berglund process with respect to the recovery of succinic acid from a mixture of sodium succinate and sodium acetate. Juetten does not discuss or suggest the use of his proposed process for the recovery of the organic acid salt. In addition, Juetten does not discuss or suggest the use of any base as a "salting-out" agent.

Methods for the purification of salts have also been proposed. U.S. Pat. No. 5,041,645, to Alon et al discloses the preparation and recovery of alkali metal citrates by the addition of an alkaline metal base or salt to citric acid solutions and recovery in solid form by the addition of a C1 to C5 alcohol to the solution to cause precipitation. The addition of alcohol is not necessary in the invention claimed herein.

U.S. Pat. No. 3,944,606 to Rieger et al discloses the extraction of alkali metal or ammonium citrates from citric acid processes including fermentation with a specific water-immiscible mixture of aliphatic amines and organic solvents and re-extraction of the resulting organic solvent mixture with an aqueous solution of an alkali metal hydroxide, carbonate or bicarbonate, ammonia or their salts.

U.S. Pat. No. 4,447,364 to Staal, discloses the preparation of a stable solution of aluminum citrate by combining a solution of aluminum chloride with a solution of citric acid with vigorous agitation. After formation of an aluminum citrate solution, sufficient alkali metal or ammonium hydroxide is added to increase the pH to 5.5 to 7.5. During addition of base agitation is continued, resulting in a solution of aluminum citrate.

The recovery process for salts claimed herein does not require organic solvent extraction or a chemical reaction.

SUMMARY OF THE INVENTION

The improved method for recovery of an organic acid salt from an impure process stream containing the organic acid and/or a corresponding salt, comprises the steps of:

a. obtaining a solution of a desired organic acid salt, concentrated to within about ten percent (by weight) of the saturation point;

b. adding a sufficient amount of a crystallizing base to the concentrated solution of the organic acid salt to produce salt crystals; and c. separating the organic acid salt crystals from mother liquor.

Preferred crystallizing bases are chosen from the group consisting of sodium hydroxide, sodium carbonate, ammonia and potassium hydroxide.

The desired salt crystallizes out of the process stream and may be separated out from the mother liquor, collected and, commonly, washed. The mother liquor may be treated further to obtain an additional yield of crystals and/or to recover the crystallizing base. Alternatively, the mother liquor may be recycled.

The improved process is particularly applicable to the recovery of an organic acid salt from a fermentation broth containing such organic acid and/or salt thereof, comprising the steps of:

a. fermenting an appropriate carbon and hydrogen source as a substrate in the presence of an appropriate microorganism to produce a fermentation broth containing an organic acid and/or salt thereof together with impurities including the biomass residue of the microorganism;

b. treating the fermentation broth to substantially remove the biomass, thereby providing a partially purified fermentation broth containing the organic acid and/or salt thereof, unreacted substrate and other impurities;

and the steps c and d in either order, c. neutralizing any residual organic acid in the partially purified fermentation broth to produce the desired organic acid salt with a neutralizing base in which the cation is the same as that of the desired salt;

d. treating the neutralized partially purified fermentation broth to provide a solution of the desired organic acid salt, concentrated to within about ten percent (by weight) of the saturation point;

e. adding a sufficient amount of a crystallizing base to the concentrated solution to produce the organic acid salt crystals; and f. separating the organic acid salt crystals from mother liquor.

Trisodium citrate and tripotassium citrate may be advantageously prepared by applying the process outlined herein to a fermentation process stream generated in the production of citric acid. The improved process may be used as a one-step purification process or as an additional purification step in conjunction with recovery processes including the traditional fermentation recovery processes, solvent extraction and lime sulfuric.

The resulting product may be further improved by drying and/or by adding an anticaking agent. Either method produces a more free flowing product.

DESCRIPTION OF THE INVENTION

The invention is an improved process for the recovery of an organic acid salt from process streams generated during manufacture of the corresponding organic acid or a salt thereof. Such manufacture often generates the organic acid initially, which is then neutralized to the desired organic acid salt.

The process defined herein is applicable to the recovery of organic acid salts such as those of volatile organic acids which are useful as flavors and perfumes, those of organic acids manufactured by fermentation for the food and beverage industry and others such as malic acid salts. Organic acids commonly obtained by fermentation include, but are not limited to, citric, lactic, succinic, acetic, itaconic, butyric and tartaric acids. Most of these latter acids, with the exception of acetic acid and citric acid, are generally prepared from a neutralized fermentation stream which results in the generation of a mixture of the acid and a salt thereof because of end product inhibition. This invention provides improved recovery of the salt form regardless of whether fermentation conditions produce predominately the acid form, a mixture of acid and salt or the acid salt itself. The process will be illustrated for a citric acid fermentation process which produces predominately the acid form. However, modifying the process claimed herein to adapt it to fermentation processes which produce an acid/salt mixture or predominantly the salt is well within the skill of those knowledgeable in the art given the disclosure and such adaptations are considered equivalent to the described herein.

Commonly the desired salt is an alkaline metal or alkaline earth metal salt which is produced by the neutralization of a process stream by a base in which the cation is the same as that in the salt of interest. This base is referred to herein as the "neutralizing base" and is often a base such as sodium or potassium hydroxide. Suitable neutralizing bases include $M(OH)_n$, $(M)_nCO_3$ and $M(HCO_3)_n$ where M is the alkali metal or alkaline earth metal cation and n is 1 or 2. Salts of interest are commonly the alkali metal or alkaline earth metal salts such as calcium, zinc, potassium, and sodium, most commonly potassium or sodium. Typically, the neutralization step is carried out after the crude organic acid solution is at least partially purified.

The process of recovery of an organic acid salt from a process stream, including but not limited to fermentation broth or a process stream associated with manufacture by fermentation, can be improved by treating a concentrated solution of the organic acid salt with a base to effect crystallization of the salt. Addition of such a base, referred to herein as a "crystallizing base" causes crystallization of the organic acid salt in high yield. Surprisingly, the cation of the crystallizing base need not be consistent with that of the neutralizing base nor of the desired end product. Preferred crystallizing bases are sodium hydroxide, potassium hydroxide, sodium carbonate, and ammonia. Ammonia may be used in the liquid or gaseous form.

The organic acid salt crystals are separated from the mother liquor, commonly by filtration such as by centrifugation. After separation of the organic acid salt crystals, the mother liquor containing crystallizing base may be recycled into the process or can be treated to provide an additional yield of salt and/or the crystallizing base may be recovered or discarded.

Improved Process as applied to Fermentation Processes

The use of the process in the recovery of organic acid salts from fermentation processes, will be used as a particular example. The fermentation broth is generally treated to remove substantially all of the biomass, most commonly by filtration.

However, the resulting partially purified fermentation broth still contains unreacted substrate and other impurities, as well as the organic acid and/or salt thereof.

The acid, or any residual acid in the case of a process which contains a mixture of acid and salt, in the fermentation broth or other impure process stream is neutralized to produce the desired organic salt and the neutralized partially purified fermentation broth is treated to provide a concentrated solution of the desired organic salt. The latter two steps may be done in either order. In addition, if the fermentation produces the salt, neutralization may not be required. All such process are considered equivalent with the one described in detail herein.

Concentration of the neutralized fermentation broth may be accomplished by any means known to one of skill in the art such as membrane filtration or evaporation, although evaporation is more commonly used. Any process which will provide a concentrated solution of the organic salt may be used, provided it does not deleteriously effect the salt of interest. The neutralized fermentation broth is generally concentrated to within about ten percent (by weight) of the saturation point at the reaction temperature used, preferably to about saturation.

Given the disclosure within and the examples shown, the degree of concentration required may be easily determined by one of skill in the art.

A sufficient amount of a crystallizing base is added to the concentrated, neutralized fermentation broth to recover the organic acid salt as crystals. The amount required to crystallize the organic acid is generally somewhere between about 1 and 50% by weight of crystallizing base to the concentrated solution, preferably between about 10 and 25%, most preferably, when working with a citrate salt, between about 15 and 20% by weight.

The organic acid salt crystals are separated from the mother liquor and are then commonly washed. The crystals may be packaged, dried and/or mixed with an anticaking agent, spray granulated or treated further, for example by additional recrystallization, or any of the other methods well known to those of skill in the art.

The mother liquor may be recycled into the process or treated to recover an additional yield of salt, which may be added to the salt obtained previously, for further treatment or packaging. An additional yield may be obtained by resin treatment, preferably by ion exchange, or by stripping. The mother liquor may also be treated to recover the crystallizing base which may be discarded or recycled. A preferred treatment will provide both a salt solution which may be added to the previously separated crystals and recyclable crystallizing base.

Any process stream may be treated as outlined above, omitting the steps of fermentation and biomass removal. Depending on the configuration of the process used, the process stream may be concentrated enough so that it need only be neutralized and crystallizing base added.

The process may also be used to obtain an organic acid itself. The salt generated by the process described herein may be converted to the acid form by a number of methods well known to those of skill in the art, including but not limited to, decomposition, ion exchange, electrodialysis and reverse osmosis. The use of the process to obtain the acid form is considered equivalent to the invention claimed herein.

The advantages of the process improvement provided herein are a simplification of the recovery process, higher productivity than traditional salt recovery processes, reduction of recycling of the mother liquor, low quantities of required reagent, low operating costs and increased product quality. Application of this process to non-fermentation manufacturing process streams is well within the skill of those knowledgeable in the art given the disclosure provided herein.

The process of the invention may be particularly advantageously applied to the recovery of trisodium or tripotassium citrate after production of citric acid by fermentation. Sodium hydroxide or potassium hydroxide, respectively, are commonly used as the neutralizing bases.

When it is desirable to have a free flowing product, the resulting organic salt product may be provided for commercial use after drying and/or may be combined with an anticaking agent. These agents are also sometimes referred to as conditioning agents. Common agents of this type are zeolites, silicates and corn starch. The choice of the agent is generally governed by the ultimate application of the product. For example, sodium citrate may be combined with zeolite for use in detergents containing zeolite as a detergent builder.

The method of the invention is further illustrated by the following examples.

EXAMPLES

Example 1

Recovery of Trisodium Citrate from Fermentation Broth.

Concentrated fermentation broth (about 50% citric acid) was neutralized to pH 8 with 50% sodium hydroxide solution (by weight) and then concentrated. 50 ml of the concentrated solution was poured into an Erlenmeyer flask with stirrer bar. The solution was stirred until it became turbid. At this point, 10 g of sodium hydroxide pellets were added as the crystallizing base. The temperature increased and trisodium citrate started to crystallize rapidly. The mixture was stirred for 2 hours and gradually cooled to 30 degrees C. The crystals were separated from the mother liquor and collected using a basket centrifuge. The recovery yield was 82% and the impurities were reduced by more than 90%.

Example 2

Recovery of Trisodium Citrate from a Process Stream

A citric acid process stream (about 50% by weight citric acid) was neutralized to pH 8 with a 50% sodium hydroxide solution and then concentrated. 50 ml of concentrated solution was poured into an Edenmeyer flask with stirrer bar. The solution was stirred until it became turbid. At this point, 10 g of sodium hydroxide pellets were added as the crystallizing base. The sodium salt of citric acid started to crystallize rapidly. The mixture was stiffed for 2 hours and gradually cooled to room temperature. The mixture was poured into a basket centrifuge and the crystals separated from the mother liquor and collected. The recovery was 92% and the impurities such as carbonizables and color were reduced by more than 90%.

Example 3

Recovery of Tri sodium Citrate from Fermentation Broth with Ammonia

Fermentation broth was neutralized to pH 9 with 50% sodium hydroxide and concentrated. 50 ml of the concentrated solution was poured into an Edenmeyer flask and stirred while ammonia, as the crystallizing base, was bubbled into the solution. The temperature increased by 10 to 20 degrees C. and external cooling was applied. After about one hour the ammonia addition was stopped. Approximately 13 g ammonia was added. The mixture was stirred for 30 minutes and cooled gradually to room temperature. The mixture was poured into a basket centrifuge and the crystals collected. The recovery was 94% and the impurities such as color and carbonizables were reduced by more than 95%.

Example 4

Recovery of Sodium Butyrate.

55 g of a 50% solution of sodium butyrate was poured into an Edenmeyer flask and stirred while ammonia, as the crystallizing base, was bubbled into the solution. The temperature increased by 15 degrees C. Approximately 3 g of ammonia was added. The mixture was stirred for one hour and cooled gradually to room temperature. The crystals were filtered and collected. More than 30% sodium butyrate was recovered by the addition of ammonia.

Example 5

Recovery of Trisodium Citrate from Fermentation Broth with Sodium Carbonate

Fermentation broth containing citric acid was concentrated to contain about 50% citric acid. To 30 g of the concentrated broth, 50% aqueous sodium hydroxide (19 g) was added until pH was 8. To the resulting mixture at 30 degrees C., 5 g of sodium. carbonate was added as the crystallizing base. The sodium salt of citric acid started to crystallize rapidly. The temperature of the mixture did not increase significantly. The mixture was stirred for 2 hours and gradually cooled to room temperature. The crystals were separated from the mother liquor by filtration. The recovery yield was 92% and the impurities were reduced by more than 90%.

It should be understood that many modifications and variations can be made in the proportions and components used herein without departing from the spirit and scope of the invention, which is solely defined by the claims.

What is claimed is:

1. An improved process for recovering an organic acid salt from an impure process stream, comprising the steps of:
   a. obtaining a solution of an organic acid salt of interest; concentrated to within about ten percent (by weight) of the saturation point;
   b. adding a sufficient amount of sodium carbonate as a crystallizing base to the concentrated solution of the organic acid salt to produce crystals of the salt; and
   c. separating the crystallized organic acid salt from mother liquor.

2. The improved process of claim 1 in which the separated mother liquor is treated to recover an additional yield of the organic acid salt.

3. The improved process of claim 1 in which the separated mother liquor is treated to recover the crystallizing base.

4. An improved process for the recovery of an organic acid salt from a fermentation broth containing such organic acid and/or salt thereof, comprising the steps of:
   a. fermenting an appropriate carbon and hydrogen source as a substrate in the presence of an appropriate microorganism to produce a fermentation broth containing a desired organic acid and/or salt thereof together with impurities including the biomass residue of the microorganism;
   b. treating the fermentation broth to substantially remove the biomass, thereby providing a partially purified fermentation broth containing the organic acid and/or salt thereof, unreacted substrate and other impurities;
   and the steps c and d in either order,
   c. neutralizing any residual organic acid in the partially purified fermentation broth to produce the desired organic acid salt with a neutralizing base in which the cation is the same as that in the desired salt;
   d. treating the neutralized partially purified fermentation broth to provide a solution of the desired organic acid salt; concentrated to within about ten percent (by weight) of the saturation point;
   e. adding a sufficient amount of sodium carbonate as a crystallizing base to the concentrated solution to produce the organic acid salt crystals; and
   f. separating the organic acid salt crystals from mother liquor.

5. The process of claim 4 in which the mother liquor separated from the organic acid salt crystals is treated to recover an additional yield of organic acid salt.

6. The process of claim 4 in which the mother liquor separated from the organic acid salt crystals is treated to recover the crystallizing base.

7. An improved process for recovering an alkali metal or alkaline earth metal salt of citric acid from an impure process stream, comprising the steps of:
   a. obtaining a solution of a desired alkali metal or alkaline earth metal citric acid salt, concentrated to within about ten percent (by weight) of the saturation point;
b. adding a sufficient amount of sodium carbonate as a crystallizing base to the concentrated solution of the alkali metal or alkaline earth metal citric acid salt to crystallize the salt; and
c. separating the salt crystals from mother liquor.

8. The improved process of claim 7 in which the separated mother liquor is treated to recover an additional yield of the desired citric acid salt.

9. The improved process of claim 7 in which the separated mother liquor is treated to recover the crystallizing base.

10. An improved process for the production of an organic acid salt from an impure process stream, comprising the steps of:
a. obtaining a solution of an organic acid salt of interest, concentrated to within about ten percent (by weight) of the saturation point;
b. adding a sufficient amount of a crystallizing base to the concentrated solution of the organic acid salt to produce crystals of the salt;
c. separating the crystallized organic acid salt from mother liquor,
d. adding an anticaking agent to the organic acid salt and/or drying to produce a free flowing product.

* * * * *